United States Patent [19]
Heckele et al.

[11] Patent Number: 5,299,562
[45] Date of Patent: Apr. 5, 1994

[54] ENDOSCOPE HAVING A CONTROLLABLE DISTAL END PIECE

[75] Inventors: Helmut Heckele, Knittlingen; Rudolf Heimberger, Oberderdingen, both of Fed. Rep. of Germany

[73] Assignee: Richard Wolf GmbH, Knittlingen, Fed. Rep. of Germany

[21] Appl. No.: 981,576

[22] Filed: Nov. 25, 1992

[30] Foreign Application Priority Data

Jan. 18, 1992 [DE] Fed. Rep. of Germany ....... 4201280

[51] Int. Cl.$^5$ ............................................... A61B 1/06
[52] U.S. Cl. ......................................................... 128/4
[58] Field of Search ....................... 128/4; 606/28, 159, 606/198; 604/95

[56] References Cited

U.S. PATENT DOCUMENTS

| | | | |
|---|---|---|---|
| 4,273,128 | 6/1981 | Lary | 606/159 |
| 4,586,923 | 5/1986 | Gould et al. | 604/95 |
| 4,779,611 | 10/1988 | Grooters et al. | 128/4 |
| 4,911,148 | 3/1990 | Sosnowski et al. | 128/4 X |
| 5,058,567 | 10/1991 | Takahashi et al. | 128/4 |
| 5,152,277 | 10/1992 | Honda et al. | 128/4 |
| 5,190,540 | 3/1993 | Lee | 606/28 |

FOREIGN PATENT DOCUMENTS

| | | |
|---|---|---|
| 0098100 | 1/1984 | European Pat. Off. . |
| 0183585 | 6/1986 | European Pat. Off. . |
| 0422842 | 4/1991 | European Pat. Off. . |
| 2130885 | 6/1984 | United Kingdom . |

*Primary Examiner*—Richard J. Apley
*Assistant Examiner*—Beverly A. Meindl
*Attorney, Agent, or Firm*—Panitch Schwarze Jacobs & Nadel

[57] ABSTRACT

An endoscope instrument shaft is provided with a bendable distal end piece, the position of which relative to the instrument shaft can be altered by means of at least one tension wire which is actuable proximally of the endoscope and is guided through a guide tube which is fixed at both ends. That side of the end piece, which side has the larger radius of curvature when the end piece is bent is constructed as a return spring and the side of the end piece having the smaller radius of curvature when the end piece is bent is pliable to facilitate bending of the end piece.

5 Claims, 2 Drawing Sheets

ENDOSCOPE HAVING A CONTROLLABLE DISTAL END PIECE

BACKGROUND OF THE INVENTION

The invention relates to an endoscope having an instrument shaft having a controllable distal end piece, the position of which relative to the instrument shaft can be altered by means of at least one tension wire, which is actuable proximally of the instrument shaft and is guided through a guide tube fixed at both ends with respect to the instrument shaft.

An endoscope of the smallest practicable external diameter, may have in addition to optics and photoconductors, a probe canal, and a distal end piece which is deflectable at least to one side. The small external diameter of such endoscopes, enable diagnosis and therapy to be carried out in parts of the body and organs thereof which are difficult to access, for example, in the bile duct, in the ureter or in a blood vessel.

German patent application No. 2,402,886 discloses a flexible fibre endoscope having a deflectable distal end. Bending of said distal end is effected by means of tension wires which are actuable proximally of the endoscope. To this end, the tension wires are threaded through rings, which loosely surround the bundle of fibres of the endoscope. The rings extend in a direction parallel to the axis of the endoscope with two orientation extensions lying diametrically opposite to each other. The orientation extensions of adjacent rings slide in opposite apertures therein to provide orientation articulation. The said extensions of the rings are shaped as circular segments, with the apertures being correspondingly shaped.

German patent specification No. 2,150,595 discloses a similar endoscope having a deflectable distal end, to that disclosed in German patent application No. 2,402,886.

There is disclosed in German patent specification No 1,766,809 also, an endoscope having a deflectable distal end. The endoscope has a distal end piece formed substantially from a helically wound strip, which is surrounded by a flexible sleeve. The helically wound strip is connected at one end to the lens attachment of the endoscope, the other end of said strip being connected to a flexible tube extending in the proximal direction. Bending of the distal end piece is effected by means of tension wires secured to the lens attachment and extending in the proximal direction to a handle part of the endoscope, which has a tension wire actuating device. The tension wires are surrounded by closely helically wound wires, the ends of which are secured, on the one hand in the actuating device and on the other hand at the distal end of said flexible endoscope tube, thereby to provide what is in structure and effect a Bowden cable. There are also provided, reinforcement wires secured to the lens attachment and in the proximal direction inside the flexible bending region of the end piece, in order to counteract contraction of the bending region upon actuation of the tension wires, and in order to prevent, as far as possible, breakage of the distal end piece, which is preferably constructed so as to be very thin, being in the form of a helically wound strip as mentioned above.

The teaching of German patent application No. 2,402,886 and German patent specification No. 2,150,595 that the deflectable distal end piece should comprise elements connected together for articulation, for example, rings, has the disadvantage that the connections needed for providing the articulation, necessitate that the bendable shaft has so large an external diameter that the endoscope cannot be used for treating said parts of the body which are difficult of access. If, however, said external diameter is kept small enough to enable said use, at the expense of reducing free the passage of the endoscope, the space therein, for example, for auxiliary instrument canals, is undesirably restricted. If, however, according to the teaching of German patent specification No. 1,776,890 the distal outer shaft consists of helically wound wire, then in order to avoid material failure upon the desired bending of the deflectable end region, additional reinforcement devices, for example, reinforcement wires, must be provided. The structure of the instrument is, therefore, undesirably complex and the free passage for auxiliary instruments or flushing and suction canals is reduced in this case also.

A distal endoscope end piece, which is deflectable by means of a Bowden cable, has the disadvantage that under the load of the tension wire, the Bowden cable rests thereon in a wave form, thereby increasing the friction between the cable and the tension wire and also shortening the endoscope shaft as a whole. Optimum bending of the distal end piece is thereby prevented.

SUMMARY OF THE INVENTION

The present invention is intended to provide an endoscope having a distal end piece which is deflectable by means of at least one tension wire, and which has a desirably small external diameter and a relative large free passage for auxiliary instruments and/or canals for fluids or gases, the deflectability of the distal end piece being improved with respect to the small size of the achievable bending radius and the precision of the control of the deflection of the end piece and the rigidity thereof in its deflected position, also being improved.

According to the present invention, the side of the end piece lying on the larger radius of bending thereof acts as a return spring upon the end piece being bent, and the side of the end piece lying on the smaller radius of bending thereof is pliant with respect to bending.

According to one embodiment of the invention said pliability with respect to bending is achieved in that the end piece is weakened on said side lying on the smaller radius of bending, by means of recesses formed therein.

An advantage of this embodiment is that the deflection means need, in practice, be only one tension wire, which takes up very little space, whereby the diameter of the endoscope shaft can be desirably small.

In this embodiment the end piece preferably comprises a tube having recesses therein, in the form of slits which run parallel to each other over part of the circumference of the tube, the remaining part of the tube, which is free of slits, constituting the return spring.

According to another embodiment of the invention, the end piece, instead of comprising said recessed tube, comprises a braided hose, the ends of which are reinforced to provide rigid, distal and annular bodies. The braided hose has on said side lying on the larger radius of bending a reinforced part connecting the annular bodies and acting as the return spring, the tension wire engages on the distal annular body and the proximal annular body is fixed. The reinforced part may be produced by welding, soldering or sticking together wires of the braided hose.

The braided hose may be so constructed at predetermined sites as to be rigid with respect to deformation, and at other sites so as to be flexible, and at further sites to provide return springs, thereby to fulfil specific requirements. The braided hose may extend from the end piece into the instrument shaft.

In order to ensure precise transfer of the control forces for deflecting the end piece of the endoscope, the guide tube, which guides the tension wire, is constructed so as to be stable with regard to tension and pressure, so that its length is unaltered during the actuation of the tension wire.

DETAILED DESCRIPTION OF PREFERRED EMBODIMENTS OF THE INVENTION

Figure 1:
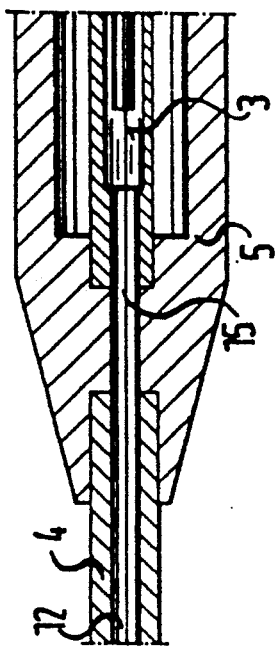
FIG. 1 is a longitudinal sectional view of a shaft of an endoscope having a deflectable end piece according to an embodiment of the present invention.
Figure 3:
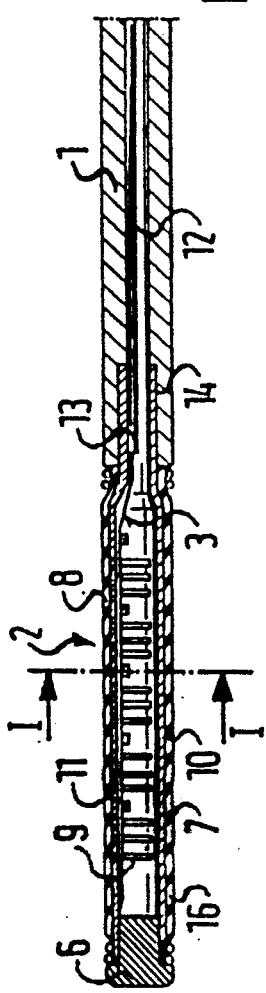
FIG. 3 shows an enlarged, fragmentary, longitudinal sectional views illustrating details of FIG. 1.
Figure 2:
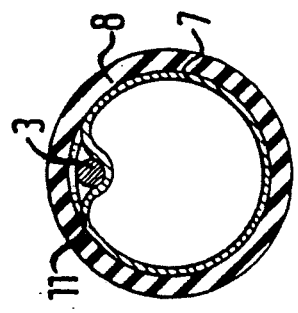
FIG. 2 is an enlarged sectional view taken on line I—I of FIG. 1.
Figure 6:
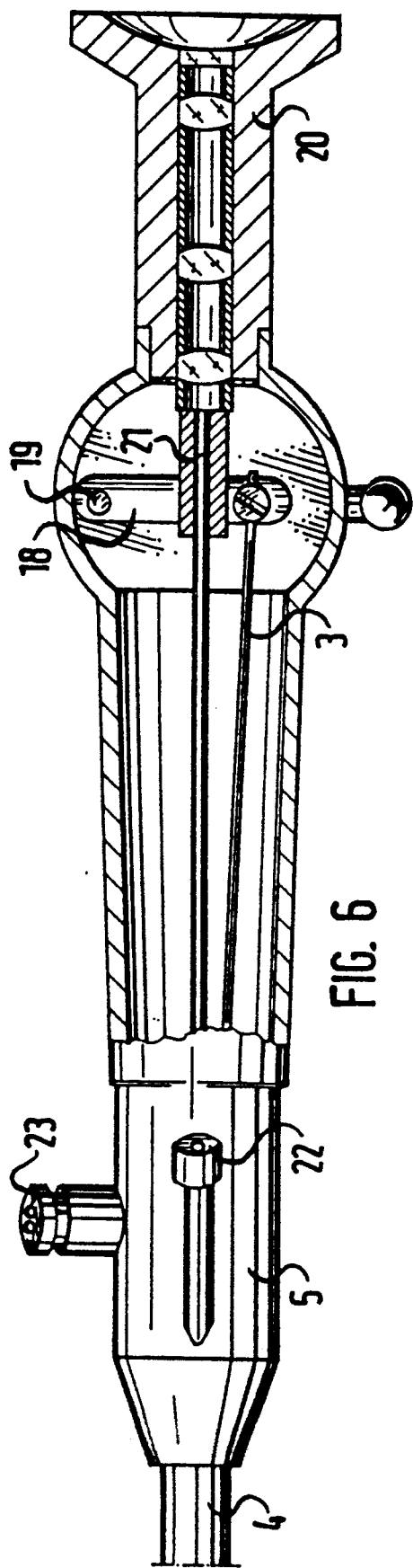
FIG. 6 is a side view of the proximal part of the endoscope, shown partially in longitudinal section.

As shown in FIGS. 1 to 3 an endoscope comprises an instrument shaft 1 having a tubular distal end piece 2 which is deflectable by means of a tension wire 3, the distal end of which is fixed to the end piece 2. The end piece 2 is connected at its proximal end to a conventional shaft part 4 which is rigid and which may be made of a synthetic resin. The proximal end of the shaft part 4 is connected to a handle housing 5 which is best seen in FIG. 6. The instrument shaft 1 may be provided with light conductors, image conductors, and suction and flushing canals, for example, in conventional fashion.

The distal end of the deflectable end piece 2 is closed by means of an endoscope tip 6. The tip 6, may, for example, be a holder for an endoscope lens (not shown) and may be perforated for connection to said canals. The end piece 2 comprises a thin walled tube 7 made of an elastic material, and a flexible outer casing 8 surrounding the tube 7.

In the embodiments of FIGS. 1 to 3 and 7, one side of the tube 7, which side has the smaller radius of curvature when the tube 7 is deflected, is formed with groups of parallel radial slits 9 which are adjacent to each other and extend over part of the circumference of the tube 7, whereby the tube 7 is flexible in two opposite directions. The side of the tube 7 opposite to said one side and which has the larger radius of curvature when the tube 7 is deflected is unrecessed so as to act as a return spring 10 and as a reinforcement of the tube 7. That side of the tube 7, which is formed with the slits 9, is also formed with projections 11 which protrude inwardly of the tube 7, between the groups of slits 9. The projections 7 snugly receive and guide the tension wire 3 as best seen in FIG. 2. At its distal end, the end piece 2 has a rigid annular section 16, and at its proximal end a rigid annular section 14. The sections 14 and 16 of the tube 7 are connected to each other axially by the radially slit part and the return spring 10 of the tube 7.

There is provided throughout the length of the shaft part 4 a thin walled guide tube 12 serving as a cover for the tension wire 3. The distal end 13 of the guide tube 12 is directly and fixedly connected to the annular section 14 of the tube 7, for example, by means of an adhesive or by soldering, or by some other conventional method. The proximal end 15 of the guide tube 12, which extends into the handle housing 5, is similarly fixedly connected thereto. The tension wire 3 is guided through the housing 5 beyond the proximal end of the guide tube 12, to a tension wire actuating device (FIG. 6) comprising a one-armed lever 18 having a pivotal axis 19, the proximal end of the tension wire 3 being fixed to the end of the lever 18 opposite to its pivotal axis 19. The lever 18 has an external operating handle projecting below, as seen in FIG. 6, the housing 5 and by means of which the lever 18 can be swung about its pivotal axis 19. The housing 5 is provided with an eyepiece 20 into which opens the proximal end of an image conductor 21. The handle housing 5 has a connector 22 for a probe canal and a connector 23 for light conductors.

Figure 5:
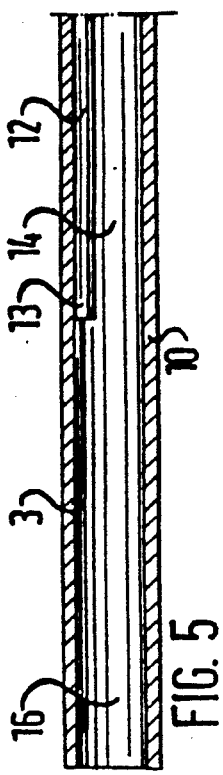
FIG. 5 is a longitudinal sectional view through the shaft end piece shown in FIG. 4.
Figure 4:
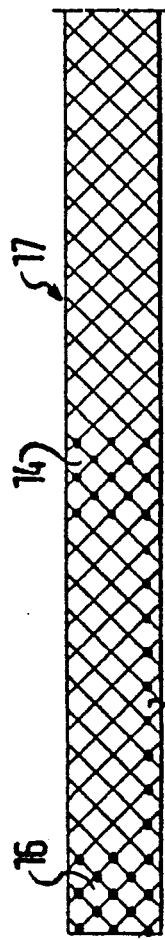
FIG. 4 is a side view of the distal end portion of the shaft of the endoscope, according to another embodiment of the invention in which said end piece is in the form of a braided hose.

In the embodiment of the end piece 2, which is shown in FIGS. 4 and 5 the end piece 2 is constructed as a braided hose 17 having at its respective ends reinforced annular, proximal and distal, sections 14 and 16 corresponding to the sections 14 and 16 of the FIGS. 1 to 3 embodiment. The braided hose 17 is flexible between its sections 14 and 16 but has one side which has the greater radius of curvature when the hose 17 is deflected, reinforced to provide the return spring 10. The reinforcement of said one side and of the annular sections 14 and 16 is achieved by welding, soldering or adhering, together, wires of the braiding of the braided hose 17. The tension wire 3 is engaged with the distal end section 16.

The deflectable distal end piece 2 can be bent to a desired extent and fully or partially straightened, by means of the handle of the lever 18. During such bending of the end piece 2 the wire 3 is loaded under tension and during such straightening of the end piece 2, the wire 3 is loaded under compression. In either case, the length of the shaft 1 remains constant and the friction between the tension wire 3 and the guide tube 12 is not increased when the curvature of the end piece 2 is altered, so that there is a minimal loss of force. The return spring 10 acts to reinforce the end piece 2 and when the tension on the wire 3 is relaxed urges the end piece 2 to its initial position.

Figure 7:
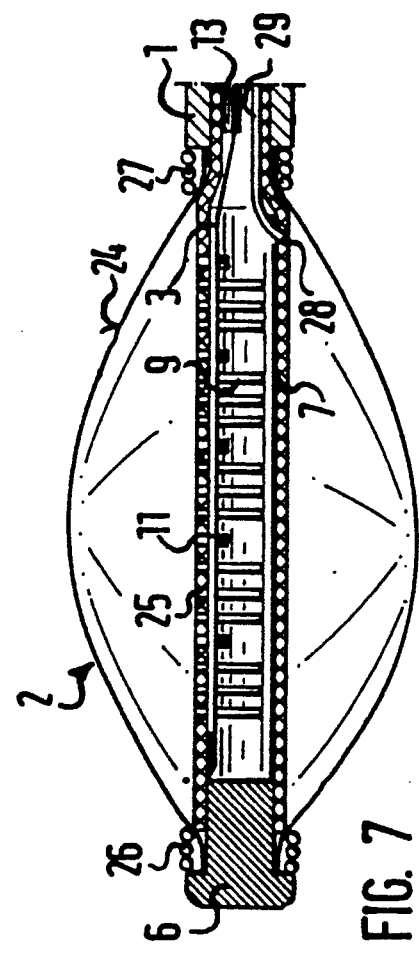
FIG. 7 is a longitudinal sectional view through the distal end piece of the endoscope of FIGS. 1 to 3, equipped with an expansible bulb for dilating a bodily cavity.

As shown in FIG. 7 an expansible bulb may be provided on the distal end piece 2 for dilating a bodily cavity. The bulb consists of an outer, flexible and expansible hose 24 and an inner hose 25 covering the slits 9. The overlapping ends of the hoses 24 and 25 are secured to the rigid annular sections 14 and 16, for example, by means of threads 26 and 27 bound thereabout. The bulb can be inflated by way of a canal 29 which opens at its distal end 28 between the hoses 24 and 25 and is connected at its proximal end to a compressed air source. When air is introduced into the bulb by way of the canal 29, the outer hose 24 rises from the inner hose 25 and when the air is evacuated from the bulb, the outer hose 24 rests tightly against the inner hose 25 again.

If the deflectable part of the end piece 2 is made of a metal having a plastic memory said flexible part may be constructed so as to have a specified anatomically favourable curvature. In this case the distal end piece can be manipulated out of its curved initial position by means of the tension wire, or if need be, by means of a plurality of tension wires.

What is claimed is:

1. In an endoscope, an instrument shaft having a controllable distal end piece which is bendable relative to the instrument shaft, a guide tube fixed at both ends relative to the instrument shaft and at least one tension wire guided through said tube and being actuable proximally of the instrument shaft to bend the distal end piece, one side of the distal end piece being bendable about a larger radius of curvature than the opposite side of the distal end piece, the one side being adapted to act as a return spring and the opposite side being pliable to facilitate bending of the distal end piece, the distal end piece comprising a braided hose, ends of which are reinforced to provide respective distal and proximal annular bodies, said one side of the distal end piece having a reinforcement means adapted to act as a return spring and to connect said annular bodies, said at least one tension wire being engaged with the distal annular body and the proximal annular body being fixed with respect to the instrument shaft.

2. The invention recited in claim 1, wherein wires of the braided hose are welded together to reinforce said one side of the distal end piece.

3. The invention recited in claim 1, wherein the braided hose extends into the instrument shaft.

4. The invention recited in claim 1, wherein the guide tube is stable with respect to tension and pressure.

5. The invention recited in claim 1, wherein an inflatable bulb is provided in the region of the distal end piece, for dilating a bodily cavity.

* * * * *